(12) United States Patent
Thompson et al.

(10) Patent No.: US 6,500,203 B1
(45) Date of Patent: *Dec. 31, 2002

(54) PROCESS FOR MAKING STENT GRAFT WITH BRAIDED POLYMERIC SLEEVE

(75) Inventors: Paul J. Thompson, New Hope, MN (US); George W. Du, Plymouth, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/321,181

(22) Filed: May 27, 1999

Related U.S. Application Data

(62) Division of application No. 08/946,906, filed on Oct. 8, 1997, now Pat. No. 5,957,974.
(60) Provisional application No. 60/036,160, filed on Jan. 23, 1997.

(51) Int. Cl.[7] .................................................. A61F 2/06
(52) U.S. Cl. ...................... 623/1.13; 156/148; 156/149; 156/172; 156/293; 156/294
(58) Field of Search .......................... 623/1.13; 156/149, 156/172, 293, 148, 294

(56) References Cited

U.S. PATENT DOCUMENTS

| | | | |
|---|---|---|---|
| 4,475,972 A | * 10/1984 | Wong | 156/167 |
| 4,553,545 A | 11/1985 | Maass et al. | |
| 4,655,771 A | 4/1987 | Wallsten | |
| 4,681,110 A | 7/1987 | Wiktor | |
| 4,732,152 A | 3/1988 | Wallsten et al. | |
| 4,738,740 A | 4/1988 | Pinchuk et al. | |

(List continued on next page.)

FOREIGN PATENT DOCUMENTS

| | | |
|---|---|---|
| EP | 0603959 A1 | 6/1994 |
| EP | 0621015 A1 | 10/1994 |

(List continued on next page.)

OTHER PUBLICATIONS

Wilson et al, "A Self Expanding Bifurcated Endovascular Graft for Abdominal Aortic Aneurysm Repair. An Initial Study in a Canine Model" ASAIO Journal 42(5), pp. M386–393, 1996.*

*Primary Examiner*—Jeff H. Aftergut
(74) *Attorney, Agent, or Firm*—Larkin, Hoffman, Daly & Lindgren, Ltd.; Frederick W. Niebuhr, Esq.

(57) ABSTRACT

A stent graft for transluminal implantation includes a resilient tubular interbraided latticework of metal or polymeric monofilaments, a tubular interbraided sleeve of polymeric multifilament yarns, and an adhesive layer between the sleeve and latticework for bonding them together. The monofilaments and multifilament yarns are arranged in respective sets of axially spaced apart and oppositely directed helices, concentric on a common axis of the stent graft. The respective braid angles of the monofilaments and multifilament yarns are carefully matched to ensure that the latticework and sleeve behave according to substantially the same relationship governing the amount of radial reduction that accompanies a given axial elongation. According to a process for fabricating the stent graft, the latticework and sleeve are braided and thermally set independently, then bonded to one another by a silicone polymer adhesive applied evenly to the latticework in a liquid spray that also incorporates an organic solvent. Especially preferred yarns are composed of essentially untwisted filaments that define non-circular yarn cross sections. Alternative stent graft constructions feature exterior and interior sleeves on opposite sides of the latticework, two or more sleeves axially spaced from one another on the same latticework, a latticework formed of a recovery metal, and a plastically deformable latticework.

46 Claims, 10 Drawing Sheets

U.S. PATENT DOCUMENTS

| | | |
|---|---|---|
| 4,760,849 A | 8/1988 | Kropf |
| 4,771,773 A | 9/1988 | Kropf |
| 4,848,343 A | 7/1989 | Wallsten et al. |
| 4,850,999 A | 7/1989 | Planck |
| 4,875,480 A | 10/1989 | Imbert |
| 4,954,126 A | 9/1990 | Wallsten |
| 4,990,151 A | 2/1991 | Wallsten |
| 5,019,090 A | 5/1991 | Pinchuk |
| 5,026,377 A | 6/1991 | Burton et al. |
| 5,061,275 A | 10/1991 | Wallsten et al. |
| 5,071,407 A | 12/1991 | Termin et al. |
| 5,084,065 A | 1/1992 | Weldon et al. |
| 5,092,877 A | 3/1992 | Pinchuk |
| 5,116,360 A | 5/1992 | Pinchuk et al. |
| 5,163,951 A | 11/1992 | Pinchuk et al. |
| 5,178,630 A | 1/1993 | Schmitt |
| 5,201,757 A | 4/1993 | Heyn et al. |
| 5,236,447 A | 8/1993 | Kubo |
| 5,282,846 A | 2/1994 | Schmitt |
| 5,356,423 A | 10/1994 | Tihon et al. |
| 5,405,380 A | 4/1995 | Gianotti et al. |
| 5,415,664 A | 5/1995 | Pinchuk |
| 5,464,408 A | 11/1995 | Duc |
| 5,476,507 A | 12/1995 | Wakabayashi et al. |
| 5,484,444 A | 1/1996 | Braunschweiler et al. |
| 5,507,769 A | 4/1996 | Marin et al. |
| 5,509,931 A | 4/1996 | Schmitt |
| 5,522,880 A | 6/1996 | Barone et al. |
| 5,534,287 A | 7/1996 | Lukic |
| 5,549,663 A * | 8/1996 | Cottone, Jr. ............... 623/12 X |
| 5,562,725 A | 10/1996 | Schmitt et al. |
| 5,575,818 A | 11/1996 | Pinchuk |
| 5,591,172 A | 1/1997 | Bachmann et al. |
| 5,591,226 A | 1/1997 | Trerotola et al. |
| 5,607,466 A | 3/1997 | Imbert et al. |
| 5,628,787 A | 5/1997 | Mayer |
| 5,628,788 A * | 5/1997 | Pinchuk .................... 623/12 X |
| 5,632,772 A | 5/1997 | Alcime et al. |
| 5,639,278 A | 6/1997 | Dereume et al. |
| 5,645,559 A * | 7/1997 | Hatchman et al. .......... 606/198 |
| 5,653,747 A | 8/1997 | Dereume |
| 5,662,703 A | 9/1997 | Yurek et al. |
| 5,667,486 A | 9/1997 | Mikulich et al. |
| 5,700,269 A | 12/1997 | Pinchuk et al. |
| 5,718,159 A * | 2/1998 | Thompson ..................... 87/2 |
| 5,758,562 A | 6/1998 | Thompson |
| 5,769,882 A | 6/1998 | Fogarty et al. |
| 5,788,626 A | 8/1998 | Thompson |
| 5,843,161 A | 12/1998 | Solovay |
| 5,891,191 A | 4/1999 | Stinson |
| 5,906,641 A * | 5/1999 | Thompson et al. ........ 623/12 X |
| 5,957,974 A * | 9/1999 | Thompson et al. ........ 623/12 X |
| 6,110,198 A * | 8/2000 | Fogarty et al. ............ 623/1.13 |

FOREIGN PATENT DOCUMENTS

| | | |
|---|---|---|
| EP | 0722701 A1 | 7/1996 |
| EP | 0855170 A2 | 7/1998 |
| GB | 1205743 | 9/1970 |
| WO | 91/10766 | 7/1991 |
| WO | 92/16166 | 10/1992 |
| WO | 94/06372 | 3/1994 |
| WO | 94/06373 | 3/1994 |

* cited by examiner

PROCESS FOR MAKING STENT GRAFT WITH BRAIDED POLYMERIC SLEEVE

This is a divisional of prior application Ser. No. 08/946,906 filed Oct. 8, 1997, now U.S. Pat. No. 5,957,974.

This application claims the benefit of U.S. Provisional Application Serial No. 60/036,160, entitled STENT GRAFT WITH BRAIDED POLYMERIC SLEEVE, filed Jan. 23, 1997.

BACKGROUND OF THE INVENTION

The present invention relates to body implantable devices and more particularly to prostheses incorporating the characteristics of stents and grafts and intended for long term intraluminal fixation.

A variety of patient treatment and diagnostic procedures involve devices intraluminally implanted into the body of a patient. Among these devices are stents as disclosed in U.S. Pat. No. 4,655,771 (Wallsten). The devices in Wallsten are tubular, braided structures formed of helically wound thread elements. The stents are deployed using a delivery catheter such as discussed in U.S. Pat. No. 5,026,377 (Burton et al.). With the stent positioned at the intended treatment site, an outer tube of the delivery catheter is withdrawn allowing the prosthesis to radially expand into a substantially conforming surface contact with a blood vessel wall or other tissue.

Thread elements or strands formed of metal are generally favored for applications requiring flexibility and effective resistance to radial compression after implantation. Metal strands can be thermally formed by a moderately high temperature age-hardening process while wound about a mandrel in the desired helical configuration. The strands, due to their high modulus of elasticity, cooperate to provide the needed strength. Strand flexibility also permits a radial compression and axial elongation of the stent that facilitates intraluminal delivery of the stent to the intended treatment site. Because the self-expanding device generally remains at least slightly radially compressed after fixation, its elastic restoring force can provide acute fixation.

The favorable combination of strength and flexibility is due largely to the properties of the strands after they have been age-hardened, or otherwise thermally treated in the case of polymeric strands. The braiding angle of the helical strands and the axial spacing between adjacent strands also contribute to strength and flexibility. Age hardening processes are described in U.S. Pat. Nos. 5,628,787 (Mayer) and 5,645,559 (Hachtman et al.).

A well known alterative stent construction features plastically deformable metallic strands in lieu of resilient strands. Plastically deformable strands can be arranged in the same helical configuration. A plastically deformable stent requires no gripping members or other feature on the catheter to maintain the stent in a reduced-radius state during delivery. However, radial expansion of the stent at the treatment site requires a dilatation balloon or other expansion means.

Regardless of whether stents are self-expanding or plastically deformable, they characteristically have an open mesh construction, or otherwise are formed with multiple openings to facilitate the necessary radial enlargements and reductions and to allow tissue ingrowth of the metallic structure. Also, such stents characteristically longitudinally expand as they radially contract, and conversely radially expand as they longitudinally contract.

Devices featuring more tightly woven strands are known. For example, U.S. Pat. No. 4,681,110 (Wiktor), discloses a flexible tubular liner insertable into the aorta to treat an aneurysm. The liner is a tight weave of flexible plastic strands, designed to elastically expand against the aneurysm to direct blood flow past the aneurysm. The tight weave is intended to minimize leakage, so that the liner can effectively shunt blood through to eliminate the aneurysmal sack from the blood path.

The Wiktor structure and others like it notwithstanding, those of skill in the art continue to encounter difficulty in providing a device that simultaneously accommodates the competing needs of low permeability, strength and flexibility for radial compression and expansion. One known approach to this problem is a combination stent graft, in which a compliant but substantially fixed-radius and tightly woven graft is sutured or otherwise coupled to a radially expandable stent. Upon release, the stent is intended to radially expand to the graft diameter. This requires a careful matching of the graft diameter with the lumen diameter at the treatment site. Otherwise, either an oversized graft is compressed between the stent and body tissue with undesirable folds or gathering of the graft material, or an undersized graft prevents the stent from radially expanding an amount sufficient to anchor the device.

Another difficulty arises from the fact that the stent layer and graft layer, even when both undergo combined radial contraction and axial elongation, behave according to different relationships governing the amount of radial reduction for a given axial increase. When the latticework elongates a greater amount for a given radial reduction, elongation of the composite structure tends to tear the bond joining the graft material to the stent. Conversely, if the graft layer undergoes the greater axial expansion, an unwanted increase in bending stiffness causes localized reductions in diameter when the stent graft is bent around tight radii. Consequently negotiation through tortuous vascular passageways becomes more difficult, and in some instances impossible.

The commercially available yarns used in textile vascular grafts are twisted for improved handling during weaving or knitting operations. The amount of twisting will depend upon certain factors including the process of yarn manufacture (e.g., continuous filament yarn or staple yarn) and desired denier. For continuous filament yarn processes, surface twisting angles will generally be between about 15–45 degrees. The multiple filaments typically form a substantially circular yarn cross-section. This limits the effectiveness of the stent graft, and increases the difficulty of matching the elongation behavior of the fabric graft, to that of the stent.

More particularly, the twisted multifilaments are tightly packed, yielding packing factors (or packing ratios) in the range of 0.7–0.9. Because of the tightly packed yarns, the tubular fabric graft has a tendency to kink when bent. The tightly packed filaments leave an insufficient void throughout the yarn cross-section for tissue ingrowth, reducing the effectiveness of long-term fixation. Further, the tightly packed yarn cross-section does not adjust itself in shape to accommodate axial elongation, thus limiting the radial contraction/axial elongation capability of the graft. The circular yarn cross-section further limits the elongation capability, because of its particular resistance to adjustments in shape.

Other disadvantages arise from the circular yarn cross-section. The yarn diameter determines the minimum thickness of the graft fabric. Yarn coverage typically is below 80 percent without additional compacting, and a fabric porosity usually is above 70 percent, again without additional compacting.

Several prostheses constructions had been suggested for composite braided structures that combine different types of strands, e.g. multifilament yarns, monofilaments, fusible materials and collagens. Examples are found in International Patent Publications No. WO 91/10766, No. WO 92/16166, No. WO 94106372, and No. WO 94/06373. Further, a highly favorable combination of strength, resilience, range of treatable lumen diameters and low permeability has been achieved by two-dimensionally woven and three-dimensionally woven composite devices featuring textile strands interbraided with either selectively cold-worked or independently thermally set structural strands, as disclosed in U.S. patent applications Ser. Nos. 08/640,062 and 08/640,091, both filed Apr. 30, 1996 and assigned to the assignee of this application. Although such devices are well suited for a wide range of procedures, there are costs and complexities inherent in interweaving different types of strands. Certain desirable modifications, e.g. providing selected areas of the device with only structural strands, are difficult.

All references cited herein, including the foregoing, are incorporated herein in their entireties for all purposes.

Therefore, it is an object of the present invention to provide a prosthesis structure that affords the advantages of stents and grafts, yet does not require an interbraiding of the structural strands characteristic of stents and the textile strands characteristic of grafts.

Another object is to provide a process for manufacturing a combination stent graft in which a structural layer and a low-permeability fabric layer undergo radial and axial enlargements and reductions, yet remain integrally bonded to one another.

It is a further object of the invention to provide a stent graft construction that facilitates selective alternate axial positioning of open-mesh areas and covered areas for shunting blood flow, to customize stent grafts for particular uses.

Yet another object is to provide, in a prosthesis featuring two or more layers formed of braided strands and of different materials, an effective bond to ensure that the layers remain integrally connected through radial expansions and contractions.

Another object is to provide a fabric graft that exhibits low permeability due to a high yarn coverage and low fabric porosity, in combination with a yarn cross-sectional porosity sufficient to enable tissue ingrowth.

A further object is to provide a stent graft with a fabric graft that is thinner and more closely matches the elongation behavior of the stent, yet affords acceptably low permeability.

SUMMARY OF THE INVENTION

To achieve the above and other objects, there is provided a process for making a stent graft, including:

a. forming a plurality of structural strands into a tubular open-mesh latticework adjustable between a nominal state and a radially-reduced axially-elongated delivery state according to a first relationship of radial reduction versus axial elongation;

b. forming a plurality of compliant textile strands into a tubular sleeve adjustable between a nominal state and a radially-reduced axially-elongated delivery state according to a second relationship of radial reduction versus axial elongation substantially equivalent to said first relationship, said latticework and said sleeve having substantially the same size and shape when in their respective nominal states;

c. applying an adhesive to at least one of said latticework and sleeve over at least a portion of the axial length of said at least one of the latticework and sleeve;

d. disposing a selected one of the latticework and sleeve within and axially aligned with the other of said latticework and sleeve so that said other surrounds said selected one, then bringing the latticework and sleeve into an engagement; and e. maintaining the latticework and sleeve in said engagement for a time sufficient for the adhesive to bond the latticework and sleeve into a composite stent graft.

The step of applying an adhesive preferably involves a curable adhesive, applied uncured to the chosen one of the latticework and sleeve. Then, maintaining the latticework and sleeve in their engagement may further involve curing the adhesive to form the bond. A preferred manner of disposing one of the latticework and sleeve within the other is to adjust the selected one to reduce its radius below that in its nominal state, axially align it within the other while the other remains in its nominal state, then radially expand the selected one to achieve engagement of the latticework and sleeve.

Preferably the structural strands are interbraided in first and second sets of helices, running in opposite directions about a common longitudinal axis, and parallel to form a first braid angle with the latticework in its nominal state. The textile strands of the sleeve preferably are similarly braided in two sets of oppositely directed helices and at a second braid angle with the sleeve in its nominal state. The first and second braid angles preferably are within about 5 degrees of one another, and more preferably are within 3 degrees of each other. In a helical weave, the braid angle is an important factor in determining the degree of radial reduction for a given amount of axial elongation. Thus, the latticework and sleeve, having substantially similar braid angles and substantially the same size and shape in their nominal states, behave according to substantially the same relationship of radial reduction versus axial elongation. Accordingly, there is no tendency in the latticework to tear free of the sleeve due to its more rapid axial elongation for a given radial reduction. Conversely, there is no unwanted increase in bending stiffness due to an axial elongation of the sleeve that exceeds that of the latticework.

The latticework and sleeve are formed independently before their joinder. Structural strands forming the latticework and textile strands forming the sleeve are wound helically about respective mandrels at their respective braid angles, then thermally set, which in the case of metallic structural strands includes age-hardening. The latticework and sleeve are joined to one another with a curable adhesive, preferably a siloxane polymer. The polymer may be dissolved in a liquid organic solvent and applied to the latticework as a spray that leaves a silicone coating or residue when the solvent evaporates. The coated latticework is radially compressed and inserted axially within the sleeve, then expands to engage the sleeve. The bond is completed by heating the latticework and sleeve sufficiently to cure the adhesive. Alternative adhesives include the polycarbonate urethanes disclosed in U.S. Pat. No. 5,229,431 (Pinchuk).

There are several approaches to matching the respective braid angles. In one approach the latticework is formed on a mandrel smaller than the mandrel used for the sleeve, and the structural strands and textile strands are wound at the same braid angle. Alternatively the respective mandrels can have the same diameter. Then, the textile strands are wound at a braid angle slightly less than that of the structural strands. Then, as the sleeve undergoes the slight radial enlargement necessary for accommodating (surrounding) the latticework in the nominal state, its braid angle increases toward a closer match with the braid angle of the latticework.

Further in accordance with the present invention, there is provided a body insertable stent graft. The stent graft includes an expandable stent formed of a plurality of interconnected structural strands, adjustable between a nominal state and a radially-reduced axially-elongated delivery state. The stent graft also includes a tubular sleeve formed of a plurality of interwoven textile strands, adjustable between a nominal state and a radially-reduced and axially-elongated delivery state. Each of the textile strands is a multifilament yarn in which the multiple filaments have a surface twist angle of at most about 15 degrees. The sleeve and the latticework have substantially the same radii when in their respective nominal states. An attachment component fixes the latticework and the sleeve together, in a selected axial alignment with one another, engaged with one another and with a selected one of the latticework and sleeve surrounding the other, whereby the latticework structurally supports the sleeve.

According to another aspect of the invention, the yarns are formed to define a non-circular cross-section with major and minor axes, with an aspect ratio (major axis:minor axis) of at least about 2.

The flatter yarns with substantially untwisted filaments provide a fabric sleeve improved in the following respects: elongation behavior that more closely matches the elongation behavior of the stent; thinner walls for a reduced delivery profile; smaller interstices between yarns achieve lower permeability; and higher yarn cross-section porosity to allow tissue ingrowth.

Although the sleeve surrounds the latticework in the more preferred approach, an alternative construction features a sleeve surrounded by the latticework. In this latter case, the sleeve should be formed on a mandrel as large as the mandrel used to form the latticework, promoting a better bond with a sleeve that tends to elastically radially expand against the surrounding latticework. According to another alterative, two polymeric sleeves are employed, with the latticework sandwiched between an exterior sleeve and an interior sleeve. A variety of enhancements are provided within the scope of the present invention, e.g. incorporating one or more radiopaque strands in the latticework or sleeve, incorporating bioabsorbable materials, providing axial runners to enhance resistance to radial compression, and coating the completed stent graft or individual strands, to reduce deployment forces and lower the inflammatory response of tissue to the implanted device.

Thus in accordance with the present invention, a stent graft incorporates a structural latticework and low-permeability sleeve, independently formed and integrally connected to simultaneously provide the structural advantages of a stent and the low permeability of a graft. The latticework and sleeve are matched to undergo substantially the same degree of radial contraction for a given axial elongation. This matching, combined with an adhesive bond of the sleeve to the latticework, ensures that the stent graft radially expands and contracts as a unitary body, despite being composed of different structural and textile layers and despite the absence of an interweaving between the different layers or between the different types of strands.

IN THE DRAWINGS

For a further appreciation of the above and other features and advantages, reference is made to the following detailed description and to the drawings, in which.

Figure 2:
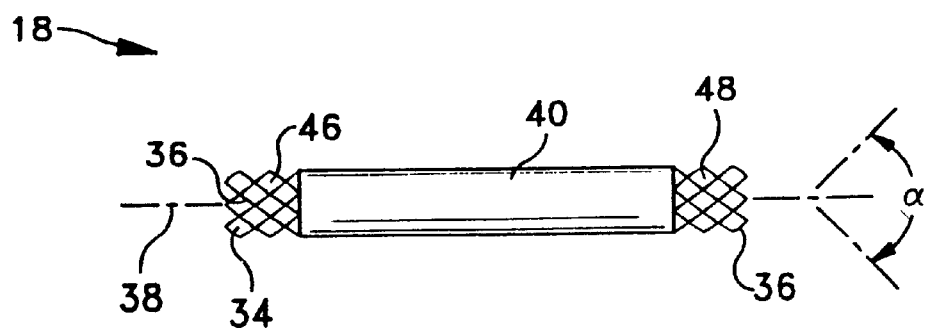
FIGS. 2 and 3 illustrate the stent graft in an unconstrained, radially expanded state, in side and end elevation, respectively.
Figure 10:
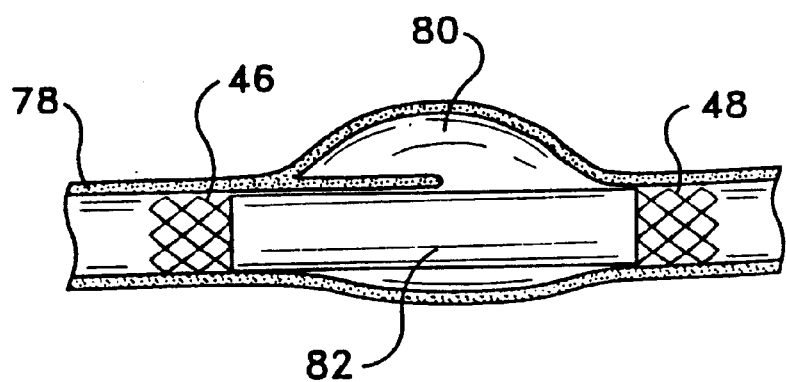
Figure 11:
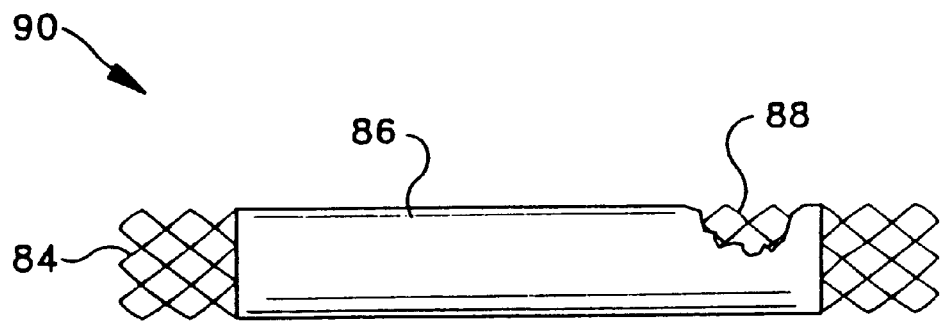
Figure 12:
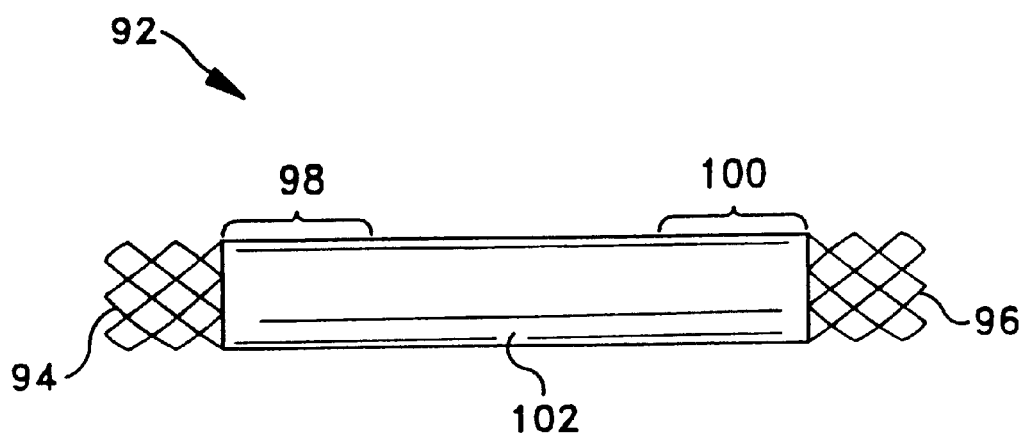
Figure 13:
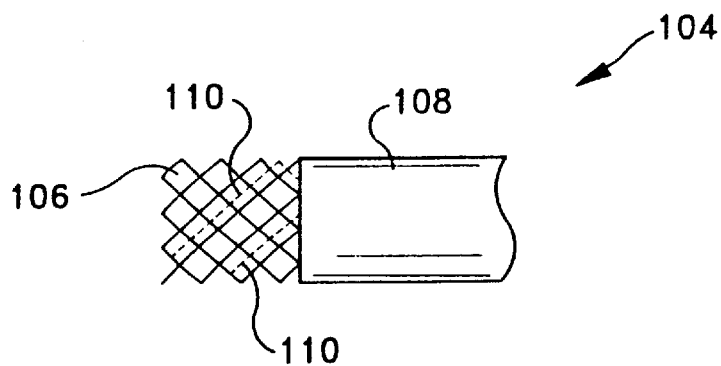
Figure 14:
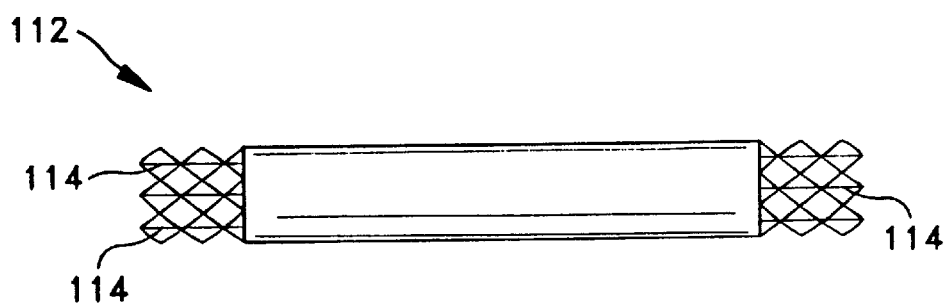
Figure 15:
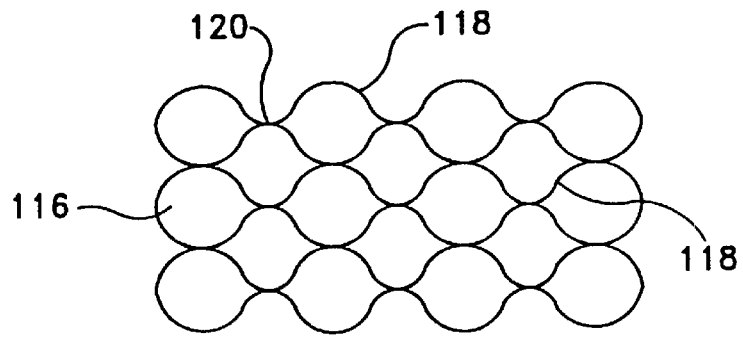
Figure 16:
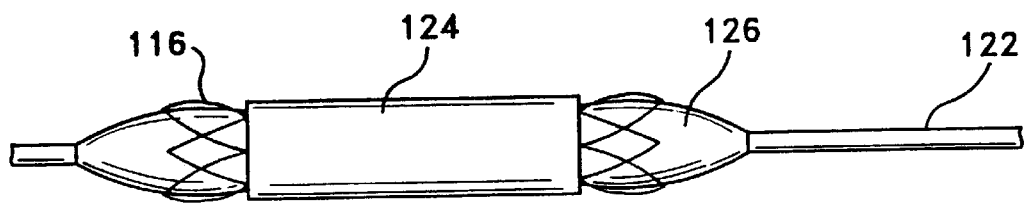
Figure 17:
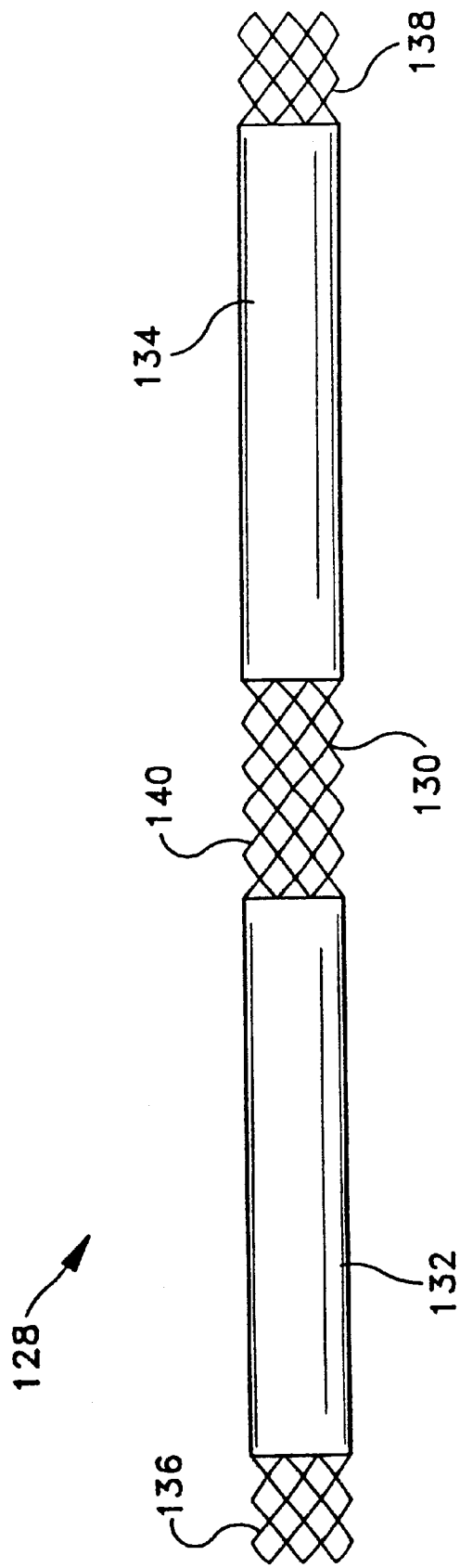
Figure 18:
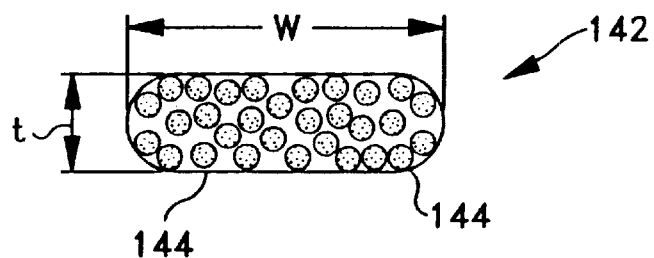
Figure 19:
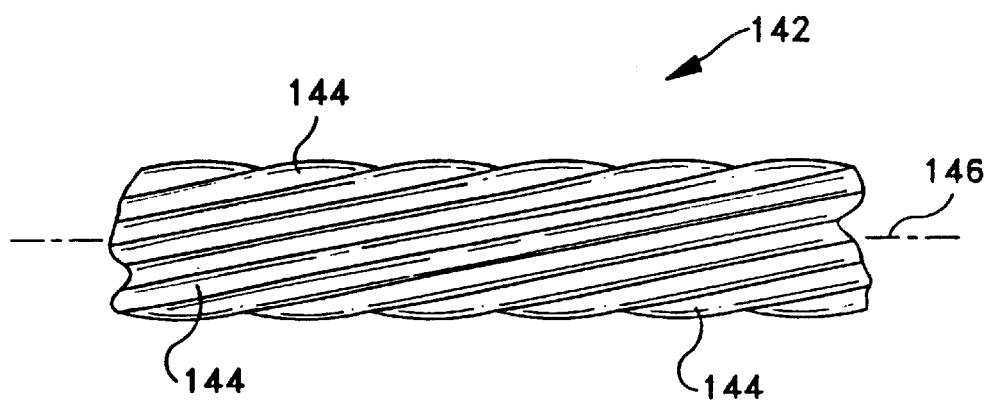

FIGS. 5–9 schematically illustrate fabrication of the prosthesis;

FIG. 10 shows the stent graft of FIG. 2 deployed within a vessel and spanning an aneurysm;

FIG. 11 illustrates an alternative embodiment stent graft with interior and exterior sleeves;

FIG. 12 illustrates another alternative stent graft with localized bonding of its latticework and sleeve;

FIG. 13 illustrates another alternative stent graft incorporating auxiliary strands;

FIG. 14 illustrates an alternative embodiment stent graft with flexible axial strands;

FIG. 15 illustrates an alternative embodiment stent graft with a plastically deformable latticework;

FIG. 16 illustrates the stent graft of FIG. 15 mounted on an alternative deployment device;

FIG. 17 shows a further alternative stent graft with selectively positioned sleeves;

FIG. 18 is a cross-sectional view of a multifilament yarn used in forming a fabric graft according to the invention;

FIG. 19 is a side elevation of a segment of the yarn; and

Figure 20:
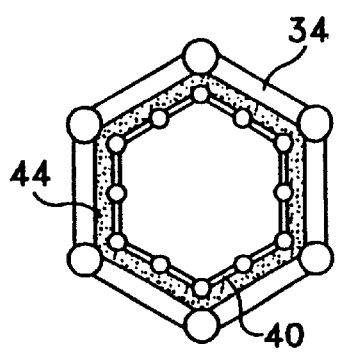

FIG. 20 is an end elevation view of a stent graft in an unconstrained, radially expanded state.

DETAILED DESCRIPTION OF THE PREFERRED EMBODIMENTS

Figure 1:
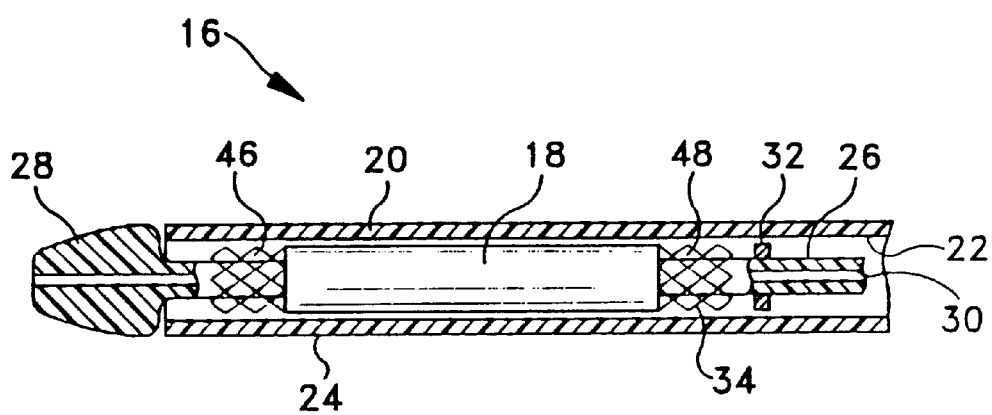
FIG. 1 is a side elevation, partially in section, showing a stent graft constructed in accordance with the present invention contained within a deployment device.

Turning now to the drawings, there is shown in FIG. 1 a deployment device 16 for delivering a stent graft 18 to an intended fixation site or treatment site within a body lumen, then controllably releasing the stent graft for radial self-expansion and fixation within the lumen.

The device includes an elongate and flexible outer catheter 20 constructed of a biocompatible polymer such as polyurethane. A central lumen 22 runs the length of catheter 20. A distal end region 24 of the outer catheter surrounds stent graft 18. An inner catheter 26 is contained within lumen 22 and runs along the entire length of the outer catheter. At the distal end of inner catheter 26 is a tapered distal tip 28 which extends beyond the outer catheter. Stent graft 18 surrounds inner catheter 26, confined between the inner and outer catheters. A lumen 30 in the inner catheter can accommodate a flexible guidewire (not shown) tracked by device 16 as it is advanced toward the treatment site.

Stent graft 18 is formed of resilient materials, and in FIG. 1 is shown elastically compressed into a radially-reduced and axially-elongated delivery state. Outer catheter 20 maintains the stent graft in the delivery state against its elastic restoring force. An annular detent 32, mounted to inner catheter 26, occupies a space between the inner and outer catheters to limit proximal travel of the stent graft relative to the inner catheter. As outer catheter 20 is moved proximally relative to inner catheter 26, the detent prevents the stent graft from following the outer catheter.

Catheters 20 and 26, while maintaining stent graft 18 in the delivery configuration, are moved transluminally to deliver the stent graft to the treatment site. Once the stent graft is positioned as intended, inner catheter 26 is held stationary while outer catheter 20 is withdrawn proximally. Inner catheter 26, due to detent 32, maintains the stent graft properly aligned as it progressively radially self-expands toward an intimate contact with tissue at the treatment site. The stent graft does not expand completely to the relaxed state, and thus exerts a residual force on surrounding tissue that tends to acutely fix the prosthesis. At this point the stent graft has a diameter much larger than the diameter of distal tip 28, so that the inner catheter and tip are proximally withdrawn to leave the stent graft in place.

Figure 3:
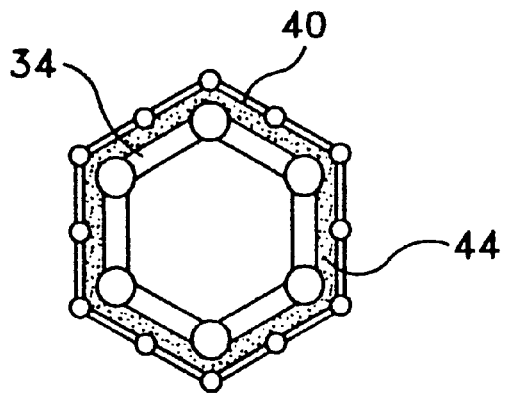

Stent graft 18 in FIGS. 2 and 3 is shown in a nominal state, in this case a relaxed state in which the stent graft is subject to no external forces. As compared to the delivery state, the prosthesis has a substantially enlarged radius and a substantially reduced axial length. The stent graft has several concentric layers which act in concert during radial expansions and contractions.

The inside layer (radially) is a latticework 34 formed of resilient monofilament structural strands 36. Strands 36 are arranged in two sets of parallel helices wound in opposite directions about a common longitudinal axis 38. Strands 36 intersect one another to define rhombotic interstices and a braid angle a bisected by axis 38. The braid angle is in the range of about 60 to 150 degrees, and more preferably 90 to 130 degrees. The number of structural strands forming the latticework can range from 10 to 120.

The braid angle is defined with reference to the nominal state of the latticework. As seen from FIG. 1, radial compression of the stent graft into the delivery state substantially reduces the braid angle. The braid angle largely determines the relationship between radial compression and axial elongation of the prosthesis. Smaller braid angles result in less axial shortening for a given amount of radial enlargement. Conversely, given a larger braid angle, the same radial expansion results in more axial shortening. For a given strand size and strength, a larger braid angle imparts greater resistance to radial compression and more positive acute fixation.

Structural strands 36 are elastic, strong, biocompatible, hemocompatible, and fatigue and corrosion resistant. Materials imparting these desired properties include certain stainless "spring" steels, cobalt-based alloys, and alloys containing titanium. Several preferred cobalt-based alloys are sold under the brand names "Elgiloy,""Phynox" and "MP35N". A particularly preferred cobalt-based alloy is a CoCrMo alloy described in U.S. patent application Ser. No. 08/640,253, entitled "Cobalt-Chromium-Molybdenum Alloy Stent and Stent Graft," filed Apr. 30, 1996 and assigned to the assignee of this application. Preferred alloys containing titanium include a recovery metal alloy of nickel and titanium sold under the brand name "Nitinol." Other titanium alloys include titanium-zirconium-niobium alloys, and a titanium-aluminum-vanadium alloy known as "TI-6A1-4V."

Monofilament structural strands 36 can be formed of polymers as well, including PET, polypropylene, PEEK, HDPE, polysulfone, acetyl, PTFE, FEP, and polyurethane. Suitable diameters for the monofilament strands range from about 0.002 inches to about 0.015 inches.

Figure 4:
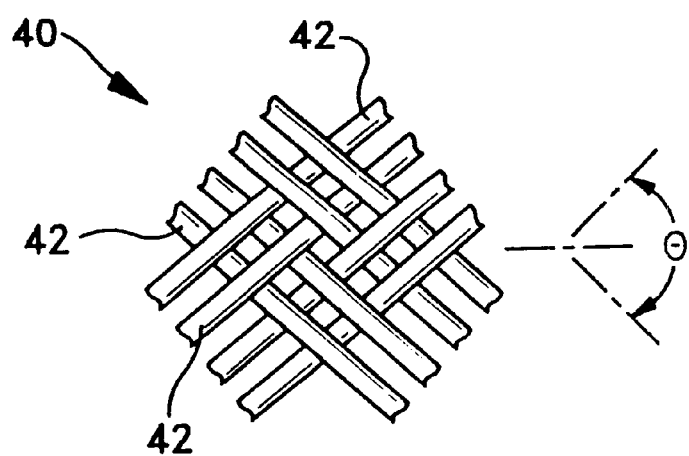
FIG. 4 is an enlarged view of the stent graft, showing the interbraiding of several textile strands.

FIG. 3 shows an exterior layer of stent graft 18 as a textile sheeting or sleeve 40, formed of multiple textile strands 42 interwoven with one another. FIG. 20 shows an alternative embodiment wherein sleeve 40 is an interior layer. As seen in FIG. 4, the textile strands are braided in a two over two pattered, although a one over one pattern or other patterns are suitable as well. The textile strands intersect one another to define a braid angle θ with sleeve 40 in a nominal state. Braid angle θ, like angle α, is bisected by axis 38. The number of yarns in the polymeric sleeve can range from 20 to 700.

Textile strands 42 preferably are multifilament yarns, although they can be monofilaments. In either case the textile strands are much finer than the structural strands, ranging from about 10 denier to 400 denier. Individual filaments of the multifilament yarns can range from about 0.25 to about 10 denier. The multifilament yarns generally have a high degree of compliance, which may or may not include elasticity. Preferably, the multifilament yarns are composed of PET (Dacron). Other acceptable materials include polypropylene, a high molecular weight polyethylene sold under the brand name "Spectra", polyurethane, HDPE, polyethylene, silicone, PTFE, polyolefins and ePTFE.

Further, it is preferable to form the multifilament yarns, such that the multiple filaments are substantially untwisted and cooperate to form an oblong or non-circular yarn cross-section. These features, and the resulting performance advantages in stent grafts that incorporate them, are discussed in more detail below, in connection with FIGS. 18 and 19.

Because of the fineness of the textile strands and close or tight weave, sleeve 40 can be microporous, yet essentially impervious to body fluids. The textile sheeting of the sleeve is highly compliant, conforming to changes in the shape of latticework 34 as stent graft 18 either radially self-expands or is radially compressed. The shape of the latticework determines the shape of the stent graft.

Despite the compliant nature of sleeve 40, proper matching of the sleeve and latticework 34 is critical to achieving high performance. In broad terms, the latticework and sleeve are matched so that when adjusted between their respective nominal and delivery states, they behave according to the same relationship of radial reduction versus axial elongation. This relationship can be expressed in terms of a percentage of radial contraction for a given percentage of axial elongation, or more succinctly a ratio of contraction to elongation. Such ratio varies with the braid angle. More particularly, at higher braid angles a given radial contraction produces a greater axial extension. In this embodiment, appropriate matching involves forming latticework 34 add sleeve 40 with the same braid angle, i.e. θ equals α. Satisfactory matching occurs if θ is within 5 degrees of α, more preferably if θ is within 3 degrees of α. A highly preferred matching involves selecting angles α and θ within one degree of each other. In different embodiments, appropriate matching may require a difference in angles θ and α. For example, where a sleeve is intended to surround a latticework, it may be advantageous to form the fabric sleeve with a braid angle θ less than the corresponding braid angle α of the latticework.

In embodiments such as illustrated in FIG. 3 where graft 40 is disposed about structural support 34, the braiding angle of textile strands 42 is preferably between 100.91 and 105.45 percent of the braiding angle of structural strands 36. In embodiments such as illustrated in FIG. 20 where graft 40 is disposed inside structural support 34, the braiding angle of textile strands 42 is preferably between 97.72 and 102.27 percent of the braiding angle of structural strands 36.

Latticework 34 and sleeve 40 are integrally secured to one another by an adhesive layer 44, more particularly silicone. The silicone adhesive forms an extremely thin (e.g. 0.005 inches, 0.12 mm) between the latticework and sleeve, adhering to both. Due to the matching of the latticework and sleeve braid angles, adhesive layer 44 is required to accommodate only slight movement of the sleeve relative to the latticework during radial expansions and contractions of the stent graft. Matching avoids a difference in rates of axial elongation that otherwise would unduly stress the adhesive layer and/or cause unwanted stiffness in resistance to bending. As a result, the stent graft is usable over a wider range of radii, elastically compressible to a smaller radius, and able to negotiate more tortuous or serpentine arterial passages.

Latticework 34 is longer than sleeve 40 and extends beyond the opposed ends of the sleeve, providing respective open-mesh end portions 46 and 48 to facilitate acute and long-term fixation. In other embodiments, latticework 34 and sleeve 40 will be congruent in length.

Figure 5:
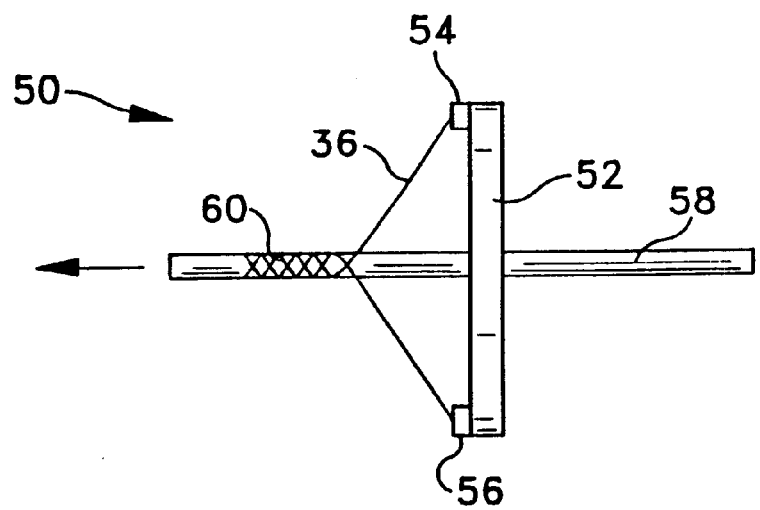

Stent graft 18 is fabricated according to several steps as illustrated in FIGS. 5–9. FIG. 5 schematically illustrates a braiding apparatus 50, including an annular carrier assembly 52. The carrier assembly supports multiple bobbins in a circular array, with two of the bobbins indicated at 54 and 56. The apparatus further includes a cylindrical mandrel 58, centered within the carrier and movable longitudinally relative to the carrier as indicated by the arrow.

In forming latticework 34, carrier assembly 52 is loaded by winding structural strands 36 onto the bobbins. The structural strands are drawn from their respective bobbins to mandrel 58 and braiding proceeds by moving the mandrel longitudinally, while at the same tme the bobbins are moved relative to one another as dictated by the desired braiding pattern. The result is an interbraiding of structural strands onto the mandrel in two oppositely directed sets of helices, as indicated at 60. The mandrel determines the diameter of the braided structure. Mandrel longitudinal speed determines the braid angle. The latticework lengths are determined by the duration of braiding, or by cutting the braided structure to desired lengths after its removal from the mandrel.

Figure 6:
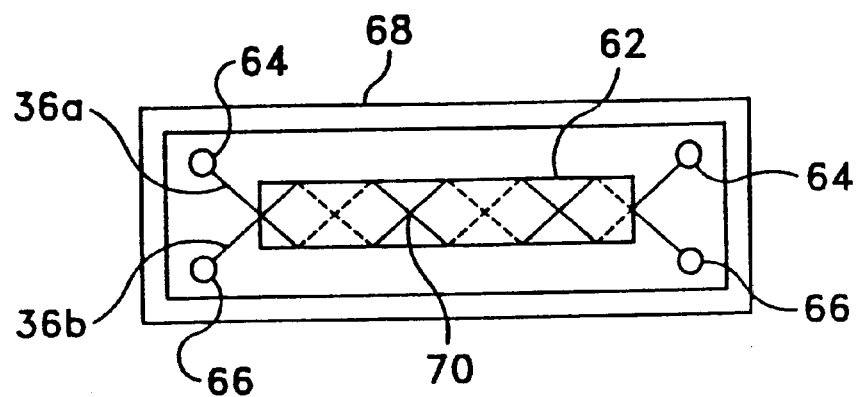

After their removal from mandrel 58, the structural strands are heat treated to determine the shape of the latticework in its nominal state. FIG. 6 illustrates two structural strands (metal monofilaments) 36a and 36b, one from each set of oppositely directed structural strands, wound about a shaping mandrel 62 and supported by respective bobbins 64 and 66. While just strands 36a and 36b are illustrated, it is to be appreciated that all of the structural strands are maintained together about the mandrel for shaping.

For metallic monofilaments, the heat treatment involves age-hardening within a furnace 68 in a vacuum or a protective atmosphere. Temperatures are within the range of about 350–1000 degrees C., with the specific temperature depending on the structural material involved. The monofilaments overlie one another to form multiple intersections, one of which is indicated at 70. The bobbins, including bobbins 64 and 66, are set to tension their respective strands during age-hardening. The appropriate duration for age-hardening varies with materials and dimensions, but can range from as brief as thirty seconds, to about five hours.

As they cool after age-hardening, structural strands 36 retain their helical shapes and collectively determine the nominal or relaxed state of latticework 36. In this embodiment the monofilament structural strands are highly resilient, i.e. deformable under external stress but elastically returning to the nominal state when free of the external stress.

Alternatively, the structural strands when constructed of a recovery metal are plastically deformable and maintained below an activation temperature, which for nitinol can be below body temperature (about 37 degrees C.). When heated to the activation temperature or above, the latticework returns to the nominal shape. In this context, the nominal shape refers to the shape to which the latticework returns when at or above the activation temperature.

In another alternative discussed below, the latticework can be formed of a plastically deformable metal other than a recovery metal. In this context, the nominal state refers to the size and shape of the latticework when first formed on the mandrel. The latticework is plastically deformable to a reduced diameter delivery state, and there is no tendency in the latticework to return to the nominal state, with or without the application of heat. The compressed latticework is plastically radially expanded toward the nominal state, with a dilatation balloon or other source of external force.

When structural strands 36 are thermoplastic rather than metallic, multiple strands are thermally set in similar fashion, but at lower temperatures. Heat forming temperatures typically range from about 100 to about 400 degrees C., and more preferably 150 to 250 degrees C. The strands are maintained at or above the heat forming temperature for a duration generally shorter than that of thermally setting metal strands, i.e. from about thirty seconds to about two hours, or more preferably five to fifteen minutes.

Sleeve 40 is formed by braiding textile strands 42 about a mandrel, again in two sets of parallel, oppositely directed helices. Braiding apparatus 50 or a similar device can be used. The multifilament yarns can be wound about mandrel 58, or another mandrel with a slightly larger diameter. A primary consideration is to select braid angle e with respect to braid angle a of the latticework, to closely match the geometrical diameter and elongation properties of the latticework and sleeve when these components are formed into the stent graft. With latticework 34 and sleeve 40 both composed of helically wound strands, this is accomplished in most cases by matching the respective braid angles, with matching on occasion involving a slight difference in the braid angles, as noted above.

Accordingly, if textile strands are wound about mandrel 58 (or another mandrel of the same diameter), braid angle θ is intentionally set a few degrees less than braid angle α. When sleeve 40 surrounds latticework 34 in the finished stent graft, it necessarily is expanded to a slightly larger radius, which entails increasing braid angle θ toward coincidence with braid angle α.

Alternatively, textile strands 42 can be braided at the same braid angle as the latticework, but on a larger diameter mandrel to account for the fact that sleeve 40 surrounds latticework 34 and the intermediate adhesive. As a final alternative these approaches can be combined, with the textile strands braided at a slightly reduced braid angle on a slightly larger mandrel.

In any event, the textile strands are thermally set while wound about a shaping mandrel, to give sleeve 40 its nominal state. The multifilament yarns are thermally set in substantially the same manner as the thermoplastic structural strands. Typically the multifilament yarns are thermally set at temperatures ranging from 150 to 250 degrees C., for times ranging from 1 to 30 minutes. More preferably, setting temperatures range from 180 to 210 degrees C., and the time for setting is about 3–5 minutes.

After the sleeve is thermally set, it is removed from the mandrel and washed ultrasonically to remove any finish on the yarn. Then, sleeve 40 is cut to the desired length using a laser, which introduces localized fusing at the ends of the strands to prevent unraveling.

Thus, prior to their joinder the latticework and sleeve are formed independently of one another. This is advantageous from the standpoint of allowing braiding and thermal setting conditions to be tailored specifically in each case to the strand structure and material involved. When latticework 34 is formed of metallic strands, the independent fabrication is essential in many cases, since the higher temperatures needed for age-hardening are above the melting points of polyesters and other materials suitable for the multifilament yarn textile strands.

Next, the completed sleeve and latticework are bonded to one another. Preferably the bond extends circumferentially about the interface between the latticework exterior surface and sleeve interior surface, over the complete axial length of the annular region over which the sleeve and latticework are adjacent one another. Further, the bond should be highly uniform over the entire region, to avoid stress concentrations and ensure a more uniform behavior of the stent graft during bending, radial expansions and radial contractions.

To this end, a siloxane polymer (silicone) is used as the adhesive and is applied as a uniformly thick coating to latticework 34. To ensure a more uniform coating, the silicone is dispersed in an organic solvent of xylene and THF (tetrahydrafuran) at a concentration of about 6% of the silicon polymer, by weight. Suitable alternative organic solvents include toluene and trichloroethylene. Suitable alternative polymers include fluorosilicone and polycarbonate urethane. Alternative adhesives include polycarbonate urethanes such as disclosed in U.S. Pat. No. 5,229,431 (Pinchuk).

Figure 7:
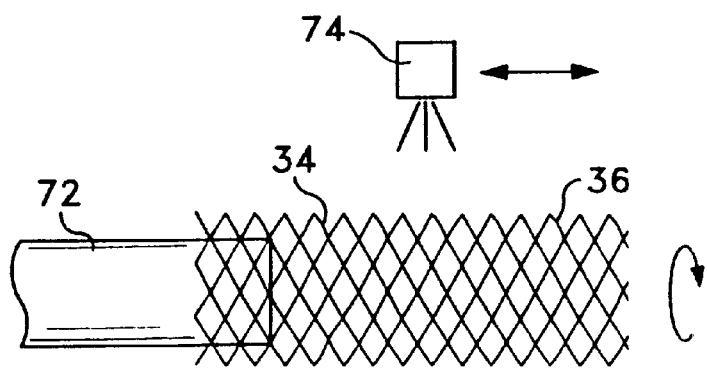
Figure 8:
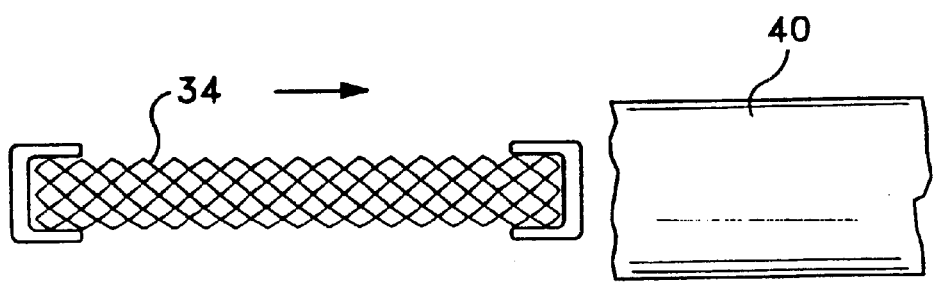
Figure 9:
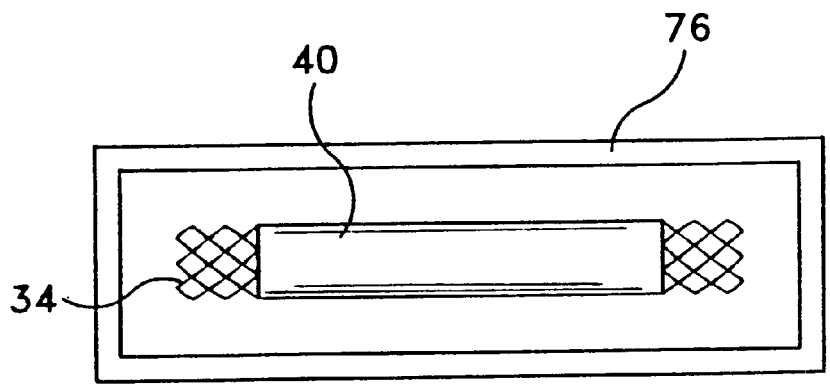

As seen in FIG. 7, latticework 34 is placed in a fixture 72 that rotates the latticework about axis 38 at a speed of about 100 rotations per minute. Then, a spraying device 74 (e.g. an air brush) is used to spray the polymer/solvent solution onto the latticework, to a uniform thickness of about 0.005 inches over the entire latticework surface. The xylene and THF are allowed to evaporate, leaving as a residue the silicone polymer, thus forming a uniform adhesive coating over the latticework.

As an alternative, a polymeric adhesive in powdered form, e.g. polypropylene or polyethylene, can be electrostatically deposited onto the latticework according to a technique known to those skilled in the art. The polymer when applied is kept below its melting point, although it may reach a fusion or glass transition temperature. Later, during bonding of the latticework and sleeve, the polymer is heated at least to its melting temperature.

As another alternative, the adhesive can be applied by a hot melt process, in which a polymer (e.g. polyurethane) is applied to the latticework in liquid form.

Next, the latticework and sleeve are assembled by axially elongating the latticework to reduce its radius, then inserting the reduced-radius latticework into sleeve 40 while the sleeve is maintained in its nominal state. Then, the silicone-coated latticework is allowed to axially shorten and radially expand into a surface engagement with the radially inside surface of sleeve 40. The thickness of the silicone coating is taken into account in the sizing of the sleeve and, latticework with respect to one another. It has been found advantageous to select the respective radii of sleeve 40 and latticework 34 so that when allowed to expand, the latticework exerts a slight radial elastic force onto the surrounding sleeve, with the sleeve preferably exerting a counteracting radially inward force upon the latticework. These counterbalancing forces improve the bond.

At this stage it is necessary to cure the silicone polymer adhesive. For this purpose, the stent graft is maintained in an oven 76 (FIG. 9) at temperatures in the range of 125–200 degrees C., for a time ranging from 20 minutes to about one hour. More preferably, the temperature is about 150 degrees C. and the time is about 30 minutes. After curing, the stent graft is removed from the oven and allowed to cool to ambient temperature. The cured silicone polymer adheres to sleeve 40 as well as the latticework, causing stent graft 18 to behave as a unitary structure, notwithstanding its three distinct layers 34, 40, and 44 as discussed above.

Thus formed, stent graft 18 combines the favorable attributes of self-expanding stents and grafts. Latticework 34 provides radial compressibility, self-expansion over a wide range of radii and a residual force sufficient for acute fixation, while sleeve 40 provides reduced permeability so that the stent graft is essentially impervious to blood and other body fluids.; As a result the stent graft is particularly well suited for treating an aneurysm. FIG. 10 illustrates fixation of stent graft 18 within a blood vessel having a vessel wall 78. Along the vessel wall is an aneurysm 80. Opposite end portions 46 and 48 of the stent graft are radially expanded into intimate contact with vessel wall 78 on opposite sides of the aneurysm. A medial region 82 of the stent graft spans the aneurysm. End portions 46 and 48 effectively fix the stent graft, due to the resilience and strength of the structural strand latticework. Fixation is enhanced by the exposed end portions. Because of the open weave latticework structure, end portions 46 and 48 more effectively engage surrounding tissue for a better acute fixation. The open structure also promotes fibrotic ingrowth, which is desirable near the end portions because it improves chronic fixation.

The following examples concern fabrication of stent grafts within the scope of the present invention.

EXAMPLE 1

The latticework is produced by setting up a 48 carrier braiding apparatus in a one over one diamond braid pattern, using 24 of the carriers. The corresponding 24 bobbins are loaded with a 0.0055 inch diameter Eigiloy wire. A 10.0 mm diameter round mandrel is placed onto the puller of the braiding device. The Elgiloy wires are threaded through their respective carriers and attached to the mandrel. The braiding apparatus is set to form a braid angle of 110 degrees. When an adequate length of the braid is formed, the latticework is removed from the mandrel. Then, the latticework is mounted onto a shaping mandrel and heat treated in a vacuum furnace, increasing the strength of the Elgiloy strands as well as inducing a more permanent memory into the strands to set the normal state of the latticework.

The polymeric sleeve is formed on a 192 carrier braiding apparatus, set in a two over two braid pattern using all 192 carriers. The corresponding bobbins are loaded with a 40 denier, 27 filament polyester yarn. A 10.5 mm diameter mandrel is inserted into the puller. The braider is operated to form a braid angle of 107 degrees. When a sufficient length of the sleeve is formed, the sleeve is removed from the braiding mandrel. Next, the sleeve is thermally set on a shaping mandrel at a temperature of 205 degrees C. for about 5 minutes. Next, the sleeve is ultrasonically cleaned to remove any finish on the yarn. The sleeve length is determined by laser cutting at the opposite ends to prevent unraveling.

An uncured silicone polymer is applied to the Elgiloy latticework, sprayed onto the latticework as a liquid solution with the silicone at six percent by weight.

The silicone solution is sprayed onto the latticework at an air pressure of about 15 psi. Spraying occurs intermittently in sets of several (preferably three) passes of the airbrush sprayer, allowing several seconds for settling between sets of airbrush passes, until an amount of solution corresponding to a desired thickness has been sprayed, i.e. approximately 26 ml for the 10 mm diameter latticework. Alternatively, the silicone solution can be applied in a continuous spray, typically lasting about 5 minutes.

The coated latticework is allowed to air dry to a tacky condition, then constrained to an axially elongated reduced radius state for insertion into the completed sleeve. Grips holding opposite ends of the latticework are moved towards one another slowly, to effect a gradual return of the latticework toward its nominal radius, and toward engagement with the surrounding sleeve. Once the latticework is completely released and engaged with the sleeve, the stent graft is cured at 150 degrees C. for thirty minutes.

EXAMPLE 2

A latticework 84 and surrounding polyester sleeve 86 are formed as before. Further, a second polyester sleeve 88, for use as an interior sleeve surrounded by the latticework, is braided on a 10.0 mm mandrel, with the braider operated to form a braid angle of 107 degrees. The latticework is axially elongated and inserted into the exterior sleeve, then allowed to gradually radially expand against the sleeve as before. Then, the second, inner polyester sleeve is axially elongated, placed within the latticework and exterior sleeve, and radially expanded into engagement against the latticework. A 9.5 mm mandrel, inserted into the interior sleeve, further urges the sleeve radially outward and into contact with the latticework. The stent graft, including the latticework and the interior and exterior sleeves, is maintained at 150 degrees C. for thirty minutes to cure the silicone adhesive. The resulting stent graft 90 is shown in FIG. 11.

EXAMPLE 3

A latticework and exterior polyester sleeve are formed as before. The latticework is sprayed with a silicone solution as before, but only along two opposite end regions, leaving a medial segment of the latticework uncovered. The latticework was axially elongated, inserted within the sleeve and allowed to radially expand against the sleeve, as in the previous examples. Oven curing was substantially the same.

The result, shown in FIG. 12, is a stent graft 92 with exposed ends 94 and 96 of the latticework coated with silicone. Opposite end bond regions 98 and 100 have axial lengths of about 17 mm, where the latticework and sleeve are bonded together. Over a medial region 102, the sleeve and latticework are adjacent one another and in surface contact, but not bonded. Where the stent graft is provided to an end user in elongated tubular form, with the intention that the end user will cut the tube to the desired lengths, bonding along the full lengths of the latticework and sleeve is recommended.

Stent grafts can be fabricated to impart a variety of desired qualities. For example, FIG. 13 shows a stent graft 104 formed with a latticework 106 of structural strands surrounded by a sleeve 108 of textile strands. An auxiliary strand 110 is interbraided with the textile strands. Strand 110 can be formed of a radiopaque material, e.g. tantalum, to improve fluoroscopic imaging of the stent graft. Alternatively, biological or bioabsorbable strands can be interwoven in this fashion.

FIG. 14 illustrates a stent graft 112 in which polyurethane monofilaments have been incorporated into the latticework as axial runners 114. To form the axial runners, the braiding apparatus is provided with an appropriate number of triaxial guide tubes arranged about the carrier assembly. One of the polyurethane monofilaments is fed into each of the triaxial guide tubes. During the curing stage, the polyurethane runners are heated sufficiently to fuse them to the remaining structure. The axial runners enhance radial recovery of the graft and reduce the tendency to unravel or fray.

Another improvement, not illustrated, is a coating of the multifilament yarn textile strands with TFE (tetrafluoroethylene) or a copolymer of TFE and silicone. The coating, which can be applied by plasma polymerization before braiding the sleeve, enhances surface properties of the yarn, e.g. by reducing friction. The resulting stent graft can be deployed with less force and inflammatory responses to the implanted stent graft may be reduced. Alternatively a plasma polymerization can occur after fabrication of the stent graft, to coat the exterior surface of the sleeve.

FIG. 15 discloses an alternative latticework 116, formed by a series of plastically deformable sinusoidal strands 118 joined to one another at multiple points 120. Latticework 116 can be plastically adjusted by a combined radial reduction and axial elongation. Strands 118 are metallic, but formed of metals much more ductile and malleable than the metals forming latticework 34 (for example). As an alternative, latticework 116 can be formed of plastically deformable strands arranged in sets of oppositely directed helices.

FIG. 16 illustrates the distal end region of a catheter 122 used to deploy a stent graft 124 including latticework 116. Stent graft 124 is governed by the structural characteristics of latticework 116 and thus remains in the axially elongated radially reduced delivery state as shown, without an additional catheter or other constraining feature. The stent graft has no tendency to elastically resume its larger radius nominal state. Thus, an auxiliary forcing feature is required to urge the stent graft, once properly positioned, toward its normal state. For this purpose a dilatation balloon 126 is mounted to catheter 122 and surrounded by the stent graft. The balloon, when inflated by the introduction of fluid under pressure through a lumen in catheter 122, radially expands the stent graft.

FIG. 17 shows a stent graft 128 with a latticework 130 surrounded by proximal and distal sleeves 132 and 134. The latticework is exposed at stent graft end portions 136 and 138, for improved acute and long-term fixation as explained, above. Each of sleeves 132 and 134 is positionable along an intraluminal location where shunting of the blood flow is desired. An exposed medial region 140 between sleeves 132 and 134 is positionable in alignment with a branch of the vessel being treated, so that stent graft 128 can provide the intended shunting without blocking flow between the main vessel and the branch between the two shunting areas.

Stent graft 128 is fabricated according to the process discussed above, i.e. with the latticework and sleeves being independently braided, then bonded with a silicone adhesive over the cylindrical regions along which the sleeves and latticework are adjacent, i.e. along the axial lengths of the sleeves. Sleeves 132 and 134, or any number of sleeves, are bonded to the latticework in a single curing operation. Sleeves 132 and 134 can be cut from the same braiding of textile strands, or braided independently, for example if different diameter sleeves are desired. In any event a stent graft can be tailored to meet specific needs by altering variables such as the number of sleeves employed, the diameter and axial length of the sleeves, and their positioning along the latticework.

As previously noted, the multifilament yarns used in commercially available textile vascular grafts are twisted yarns, i.e. the multiple filaments making up the yarn have surface twist angles in the range of about 15 degrees to about 45 degrees. The multiple filaments characteristically define a circular yarn cross-section. This structure has been favored, because such yarns are structurally stable and lend themselves well to handling by the equipment used in weaving and knitting processes. With respect to stent grafts, especially of the self-expanding type, this yarn structure is a detriment to stent graft performance in several respects.

The high degree of filament twisting can cause kinking of the fabric when the stent graft is bent, which limits the curvature of vessels in which the stent graft can be deployed and implanted. In twisted yarns the multifilaments are tightly packed, with the packing factor (ratio of cross-sectional area of the combined filaments to the cross-sectional area of the yarn as a whole) in the range of 0.7–0.9. Thus the void, or the accumulation of interstices between adjacent filaments, is insufficient for tissue ingrowth. Fibrotic ingrowth is desired, because it contributes to an effective chronic fixation of the stent graft.

The tight packing of the filaments and circular yarn cross-section combine to unnecessarily limit the elongation capabilities of the fabric graft, because the tightly packed yarn lacks the capability of adjusting itself in cross-sectional profile during elongation.

The circular cross-section sets a minimum dimension for the stent graft, in that the fabric graft wall is preferably at least as thick as two yarn diameters. The fabric coverage is undesirably low because of the circular yarn cross-section, i.e. usually below 80 percent without additional compacting. The fabric porosity is undesirably high, usually above 70 percent without additional compacting.

The above disadvantages are overcome according to a preferred embodiment of the present invention, namely construction of the graft or sleeve with an essentially untwisted (or slightly twisted) multifilament yarn in which the filaments have a surface twisting angle of at most about 15 degrees. Further, the yarn is formed with a preferred, non-circular cross-section. As seen in FIG. 18, a textile strand or yarn 142 is composed of multiple filaments 144 arranged to define a yarn cross-sectional shape with an aspect ratio slightly greater than three. In more general terms, the aspect ratio is defined as:

$$f=w/t$$

where f is the aspect ratio, w is the cross-sectional width, and t is the cross-sectional thickness. The values w and t also can be thought of as respective major and minor axes of the yarn cross-section. The yarn as shown in FIG. 18 consists of untwisted fibers having circular cross-sections. In cases where the fibers are twisted, their cross-sections would appear eliptical. While satisfactory non-circular cross-sections can have aspect ratios up to about 20, preferred aspect ratios are in a range from about 2 to about 12.

FIG. 19 illustrates a segment of multifilament yarn 142, showing the surface twist angle of the multiple filaments that make up the yarn. Filaments 144 are helically arranged, and the surface twist angle is the angle of incline of the filament with respect to a longitudinal axis 146 of the yarn, in the same sense that braid angles α and θ are defined with respect to longitudinal axes of their respective tubular structures. The preferred twist angle of the filaments is at most about 5 degrees, significantly less than surface twist angles typical of conventional twisted yarns, typically with surface twist angles in the range of 15–45. Because of the reduced twist angle, yarn 142 can be formed with a considerably reduced packing factor. The result is more interstitial space within the yarn for fibrotic ingrowth, for more secure chronic fixation of the sleeve.

The use of multifilament yarns with the preferred non-circular cross-sections, and in which the filaments are essentially untwisted, provides several performance advantages. The lack of any substantial twisting leads to a wider range of fiber packing, with packing factors ranging from 0.5–0.9. The fiber packing factor k is defined as:

$$k=n(Af)/(Ay)$$

where n is the number of filaments or fibers in the yarn, Af is the cross-sectional area of each fiber, and Ay is the total cross-sectional area of the yarn. Selection of lower packing factors within this range, i.e. 0.5–0.7, allows the yarn cross-sectional area to change in response to changes in the stent graft; i.e. shrink in response to elongation of the fabric sleeve, and expand as the sleeve recovers toward its nominal length. Further, the more loosely packed filaments provide a more porous yarn with increased voids or interstices between filaments, enabling tissue ingrowth for improved long-term fixation of the graft.

The preferred non-circular yarn cross sections cooperate with the more loosely packed filaments to improve elongation properties. More particularly, the yarn cross-sectional shape can change, narrowing as the sleeve is elongated, then widening as the sleeve recovers towards its nominal length.

Further, the higher aspect ratio, "flattened" yarns can be made with a reduced thickness without diminishing strength, since strength is a function largely of the yarn cross-sectional area. With the yarn's thickness being less than one-third of its width, as illustrated in FIG. 18, the result is a substantial reduction in thickness of the fabric sleeve. This feature, in cooperation with improved elongation capability, enables delivery of the stent graft to treatment sites in narrower vascular passages. Yet another benefit of the increased aspect ratio is the combination of better fabric coverage and reduced fabric porosity, thus reduced permeability to water and other fluids.

To summarize, the lack of any substantial filament twisting and resultant lower packing factors, and higher aspect ratios for the yarn cross sections, yield the following advantages:

1. water permeability below 2000 ml/min/cm$^2$ (at 120 mm Hg pressure), due to a yarn coverage or fabric coverage of greater than 90 percent and a porosity of less than 60 percent;
2. a substantially thinner fabric sleeve (e.g., average thicknesses less than 0.25 mm), permitting a smaller delivery profile and implantation in smaller diameter arteries; and
3. improved elongation capability in the sleeve, e.g. greater than 60 percent elongation depending on the braid angle, to better match the elongation properties of self-expanding stents.

The advantages are better understood upon consideration of the following two examples which, while based on a mathematical model, nonetheless illustrate the performance improvements realized when the fabric sleeve of a stent graft is formed with multifilament yarns having reduced filament twist, low filament packing and non-crcular profiles.

EXAMPLE 4

Textile strand: a twisted, 80 denier PET multifilament yarn, having an aspect ratio of 1, and a packing factor of 0.75.

Fabric sleeve: inside diameter of 10 mm, braid angle of 110 degrees, 192 yarn ends, fabric thickness of 0.0073 inches, yarn coverage of 66 percent, and fabric porosity of 76 percent.

Table 1 illustrates structural changes in the fabric sleeve and yarn, accompanying radial contraction and axial elongation of the sleeve:

TABLE 1

| Inner Diameter | Fabric Elongation | Braiding Angle | Fabric Thickness | Yarn Coverage | Fabric Porosity | Yarn Aspect Ratio | Fiber Packing Factor |
|---|---|---|---|---|---|---|---|
| 10.00 mm | 0% | 110N | 0.0073" | 66% | 76% | 1.0 | 0.75 |
| 9.00 mm | 18% | 95N | 0.0073" | 71% | 73% | 1.0 | 0.75 |
| 8.00 mm | 32% | 82N | 0.0073" | 72% | 73% | 1.0 | 0.75 |
| 7.00 mm | 43% | 70N | 0.0073" | 74% | 72% | 1.0 | 0.75 |
| 6.00 mm | 52% | 59N | 0.0067" | 75% | 66% | 1.0 | 0.80 |
| 5.85 mm | 53% | 57N | 0.0066" | 75% | 65% | 1.0 | 0.91 |

EXAMPLE 5

Textile strand: 40 denier PET multifilament yarn, without any substantial twisting of the filaments, with a yarn aspect ratio of 3.66 and a filament packing factor of 0.50.

Fabric sleeve: inside diameter of 10 mm, braid angle of 110 degrees, fabric thickness of 0.0032 inches, yarn coverage of 95 percent, and fabric porosity of 60 percent.

Table 2 illustrates structural changes in the fabric sleeve and the yarn, as the fabric sleeve is radially contracted and axially expanded.

TABLE 2

| Inner Diameter | Fabric Elongation | Braiding Angle | Fabric Thickness | Yarn Coverage | Fabric Porosity | Yarn Aspect Ratio | Fiber Packing Factor |
|---|---|---|---|---|---|---|---|
| 10.00 mm | 0% | 110N | 0.0032" | 95% | 60% | 3.66 | 0.54 |
| 9.00 mm | 18% | 95N | 0.0032" | 96% | 63% | 3.92 | 0.50 |
| 8.00 mm | 32% | 82N | 0.0032" | 96% | 63% | 3.85 | 0.50 |
| 7.00 mm | 43% | 70N | 0.0032" | 95% | 61% | 3.66 | 0.54 |
| 6.00 mm | 52% | 59N | 0.0032" | 94% | 58% | 3.16 | 0.60 |
| 5.00 mm | 59% | 48N | 0.0032" | 92% | 53% | 2.62 | 0.72 |
| 4.00 mm | 65% | 38N | 0.0046" | 77% | 65% | 1.11 | 0.84 |
| 3.83 mm | 66% | 36N | 0.0043" | 78% | 61% | 1.15 | 0.91 |

As is clear from comparing Table 2 with Table 1, the use of essentially untwisted multifilament yarns defining non-circular yarn cross-sections considerably improves the resulting fabric sleeve. Axial elongation is 66 percent in the preferred sleeve, compared to 53 percent elongation in the sleeve composed of conventional, twisted yarn. The inner diameter at full elongation is substantially less for the preferred sleeve, i.e. 3.83 mm as compared to 5.85 mm. Thus, the preferred sleeve, when elongated to its reduced-radius delivery state, can travel through much narrower vascular passages, and enables use of a smaller profile delivery device.

The preferred device has a much thinner fabric wall, both in the nominal state (no axial expansion) and when axially expanded. This augments the improved elongation capability, to further reduce the diameter of the sleeve in the delivery state.

In the preferred sleeve, the yarn coverage or fabric coverage is significantly higher (95 percent versus 66 percent), and the fabric porosity is significantly lower (60 percent versus 76 percent), resulting in lower permeability.

Because the filaments in the preferred yarn are less tightly packed (packing factor before extension of 0.54 versus 0.75), porosity on a "micro" scale, i.e. throughout the yarn cross-section, is substantially greater, resulting in more tissue ingrowth, and thus improved chronic fixation.

Finally, the preferred sleeve requires less material (40 denier yarn as compared to 80 denier yarn).

As the preferred sleeve is elongated, the yarn cross-section aspect ratio is reduced from 3.66 before elongation to 1.15 at complete elongation. This illustrates the extent to which the yarn cross-section undergoes changes in its profile to accommodate the axial elongation. By contrast, the less preferred circular cross-sectional yarn retains its aspect ratio of unity during elongation. The fabric thickness of the sleeve employing the twisted yarn remains essentially the same during axial elongation, although slightly decreasing near the end. The fabric thickness of the preferred sleeve also remains constant through most of the axial elongation, but increases substantially near the end because of the reduced yarn diameter resulting from increased fiber packing.

In the twisted-yarn sleeve, yarn coverage increases with axial elongation, while fabric porosity decreases. In the preferred sleeve, yarn coverage decreases significantly near the end of axial elongation, while fabric porosity remains generally constant. In both sleeves, axial elongation increases the packing factor.

The above trends and comparative values notwithstanding, it is to be understood that fabric sleeve performance is governed by yarn coverage, fabric porosity, yarn aspect ratio and packing factor at or near the nominal state, i.e. with little or no axial elongation.

Further in accordance with this invention, parameters relating to the yarns and fabrics can be tailored to achieve desired physical properties.

In general, thinner walls for the fabric sleeve are preferred, so long as the fabric sleeve meets water permeability, longitudinal strength and radial burst strength requirements. Yarn cross-sectional aspect ratios in the preferred range of 2–12 permit substantial thinning of the fabric sleeve without sacrificing longitudinal or radial strength.

The filament or fiber packing factor should be optimized to balance the desire for tissue ingrowth with the need for graft permeability. The filament packing in textured yarns is optimal at packing factors of 0.50–0.55 in the unconstrained state. Flat yarns are characterized by higher optimum densities, with favored packing factors from about 0.60 to about 0.65 in the unconstrained state.

The selection of yarn cross-sectional aspect ratios also require optimizing. Higher aspect ratios lead to improved axial elongation properties. However, they also reduce the degree of yarn (filament) interlocking, thus tending to reduce fabric stability. The preferred aspect ratio range of 2–12 has been found to satisfy these competing needs, with the lower end of the range favoring stability while the higher end favors enhanced elongation.

The yarn coverage ratio preferably is as high as possible to achieve minimum yarn interstices, while fabric porosity is kept low to meet water permeability requirements.

The number of yarn ends should be fixed after determining several other factors, including braid angle, sleeve diameter, fabric thickness, yarn linear density, packing factor, and aspect ratio.

Table 3 illustrates several examples of fabric sleeves for use in stent grafts. In all cases, the textile strands have a packing factor of 0.54, and are braided at a braid angle of 110 degrees.

TABLE 3

| Inner Diameter | Number of Yarn Ends | Yarn Linear Density | Fabric Thickness | Yarn Coverage | Fabric Porosity | Yarn Aspect Ratio |
| --- | --- | --- | --- | --- | --- | --- |
| 6 mm | 72 | 70 | 0.0031" | 98% | 55% | 6.53 |
| 6 mm | 96 | 50 | 0.0032" | 97% | 58% | 4.62 |
| 6 mm | 120 | 40 | 0.0034" | 94% | 62% | 3.15 |
| 6 mm | 144 | 30 | 0.0032" | 93% | 64% | 2.69 |
| 12 mm | 192 | 50 | 0.0032" | 97% | 58% | 4.62 |
| 24 mm | 352 | 60 | 0.0035" | 97% | 58% | 4.56 |
| 40 mm | 512 | 70 | 0.0034" | 98% | 56% | 5.45 |

Thus in accordance with the present invention, a stent graft is formed with distinct layers to provide the structural advantages of stents with the capacity of grafts for shunting blood and other body fluids. The stent graft is adjustable in size by simultaneous radial reduction and axial elongation, or simultaneous radial enlargement and axial shortening. The separate layers are configured to behave according to substantially the same relationship of radial change with respect to axial change, so that the graft behaves as a unitary structure during radial enlargements and reductions. The layered construction involves independent formation of latticework and microporous sleeves followed by their bonding, a process that reduces cost and promotes a customizing of stent grafts through selective positioning of sleeves to leave areas of the latticework exposed.

What is claimed is:

1. A process for making a medical device, including:
   braiding a plurality of structural strands into a tubular open latticework in which the strands form multiple first intersections and define a first braid angle when in a nominal state, wherein the structural strands along the length of the tubular open latticework are free of bonding to one another at the first intersections, said tubular open latticework being adjustable between the nominal state and a radially-reduced axially-elongated state according to a first relationship of radial reduction versus axial elongation;
   braiding a plurality of compliant textile strands into a tubular sleeve in which the textile strands form multiple second intersections and define a second braid angle substantially the same as said first braid angle when in a nominal state, wherein the textile strands along the length of the tubular sleeve are free of bonding to one another at the second intersections, said tubular sleeve being adjustable between the nominal state and a radially-reduced axially-elongated state according to a second relationship of radial reduction versus axial elongation substantially equivalent to said first relationship; and
   attaching a selected one of the latticework and sleeve within and in an axial alignment with the other of said latticework and sleeve so that said other surrounds the selected one.

2. The process of claim 1 wherein:
   said forming of structural strands includes arranging the structural strands as first and second sets of helices wound in opposite directions about a common longitudinal axis, thereby forming rhombic interstices between adjacent structural strands.

3. The process of claim 2 wherein:
   said forming of textile strands includes arranging the textile strands as third and fourth sets of helices wound in opposite directions at the second braid angle when the sleeve is in its nominal state.

4. The process of claim 3 wherein said second braid angle is between 100.91 and 105.45 percent of said first braid angle and the sleeve is attached about and in axial alignment with the latticework.

5. The process of claim 3 wherein said second braid angle is between 97.72 and 102.27 percent of said first braid angle and the sleeve is attached within and in axial alignment with the latticework.

6. The process of claim 2 wherein:
   said structural material is thermally formable, and said forming of structural strands further includes winding the structural strands around a selectively sized first mandrel, then heating the strands while so wound to a heat forming temperature sufficient to thermally impart a nominal size and shape for the latticework when in its nominal state; and
   wherein said textile strands are thermally formable, and said forming of textile strands further includes winding the textile strands around a selectively sized second mandrel, then heating the textile strands while so wound to a second heat forming temperature sufficient to thermally impart a nominal size and shape to the sleeve when in the nominal state.

7. The process of claim 6 wherein:
   said selected one of the latticework and sleeve is the latticework, and said disposing includes positioning the latticework within and surrounded by the sleeve.

8. The process of claim 7 wherein:
   said first mandrel has a diameter less than that of said second mandrel.

9. The process of claim 2 wherein:

said forming of structural strands further includes heat setting the structural strands when they are wound about a first mandrel at a first braid angle to determine a nominal latticework size and shape, said forming of textile strands includes thermally setting the textile strands when they are wound about a second mandrel at a second braid angle to determine a nominal sleeve size and shape.

10. The process of claim 9 wherein:
the second mandrel has a diameter greater than that of the first mandrel, and said first and second braid angles are within one degree of one another.

11. The process of claim 9 wherein:
said first and second mandrels have substantially the same diameters, and the first braid angle is larger than the second braid angle.

12. The process of claim 1 further including:
prior to said disposing, applying an adhesive to at least one of the latticework and the sleeve over at least a portion of its axial length, wherein said forming an attachment includes maintaining the latticework and the sleeve in said engagement for a time sufficient for the adhesive to bond the latticework and the sleeve to form the composite stent graft.

13. The process of claim 12 wherein:
said applying includes dissolving the adhesive in a liquid solvent, spraying the combined solvent and adhesive onto the at least one of the latticework and sleeve, and then evaporating the solvent whereby said coating is formed of a residue consisting essentially of the adhesive.

14. The process of claim 13 wherein:
said applying further includes providing the adhesive in the form of a siloxane polymer and dissolving the siloxane polymer in an organic solvent at about 6 percent siloxane polymer by weight.

15. The process of claim 13 wherein:
said adhesive is heat curable, and said forming an attachment includes maintaining the composite stent graft at a temperature of about 125–200 degrees C. for about 20 minutes to one hour.

16. The process of claim 12 wherein:
said adhesive is curable, and applied uncured to said at least one of the latticework and sleeve; and
said forming of the attachment includes curing said adhesive to bond the latticework and sleeve.

17. The process of claim 16 wherein:
said applying includes electrostatically depositing an adhesive onto the at least one of said latticework and sleeve.

18. The process of claim 16 further including:
after said curing, plastically deforming the latticework to reduce the radii of the latticework and the sleeve to their respective states.

19. The process of claim 1 wherein:
said disposing includes adjusting the selected one of the latticework and sleeve to reduce its radius below that in its nominal state, axially aligning the selected one with the other while the other remains in its nominal state, and then radially expanding the selected one toward said engagement with the other.

20. A stent graft formed according to the process of claim 1.

21. The process of claim 1 wherein:
the forming of the compliant textile strands into a tubular sleeve comprises imparting to the sleeve in the nominal state a diameter substantially the same as a corresponding diameter of the tubular open latticework in the nominal state.

22. A process for making a medical device, including:
providing a tubular stent comprised of a plurality of structural strands and adjustable between a nominal state and a radially-reduced axially-elongated state according to a first relationship of radial reduction vs. axial elongation;
winding a plurality of complaint and thermally formable textile strands, to form a tubular sleeve having substantially the same size and shape as the stent in its nominal statem and heating the sleeve to a heat forming temperature sufficient to thermally impart said size and shape to the sleeveas the nominal size and shape of the sleeve when in a nominal state, wherein the sleeve is adjustable between said nominal state and a radially-reduced axially-elongated state according to a second relationship of radial reduction vs. axial elongation substantially equivalent to said first relationship, and provides a graft;
disposing a selected one of the stent and the sleeve within and in an axial alignment with the other of the stent and sleeve, so that said other surrounds the selected one, then bringing the stent and sleeve into an engagement; and
while maintaining the stent and sleeve in said engagement, binding the latticework and the sleeve together.

23. The process of claim 22 further including:
applying an adhesive to at least one of the stent and the sleeve over at least a portion of its axial length; and
wherein said binding includes maintaining the sleeve and the stent in said engagement for a time sufficient for the adhesive to bond the sleeve and the stent.

24. The process of claim 23 wherein:
said adhesive is a curable adhesive, and is applied uncured to the at least one of said stent and sleeve; and
said binding of the stent and sleeve includes curing the adhesive.

25. The process of claim 22 wherein:
said disposing includes adjusting said selected one of the stent and sleeve to reduce its radius below that in its nominal state, axially aligning the selected one while radially reduced with the other of said stent and sleeve while said other remains in its nominal state, then radially expanding said selected one toward said engagement with the other.

26. The process of claim 22 wherein:
said disposing places the stent within and surrounded by the sleeve.

27. The process of claim 22 wherein:
said structural strands are thermally formable, and said providing a tubular stent comprises winding the structural strands around a selectively sized first mandrel, then heating the strands while so wound to a first heat forming temperature sufficient to thermally impart a nominal size and shape for the stent when in its nominal state.

28. The process of claim 27 wherein:
said winding a plurality of textile strands comprises winding the textile strands around a selectively sized second mandrel.

29. The process of claim 22 wherein:
said providing a tubular stent comprises arranging the structural strands as first and second sets of helices wound in opposite directions about a common longitudinal axis, thereby forming rhombic interstices between adjacent structural strands.

30. The process of claim 29 wherein:

said arranging of the structural strands further includes heat setting the structural strands when they are wound about a first mandrel at a first braid angle to determine a nominal stent size and shape.

31. The process of claim 30 wherein:

said winding a plurality of textile strands comprises arranging the textile strands as third and fourth sets of helices wound in opposite directions at a second braid angle when the sleeve is in its nominal state; and said heating the tubular sleeve includes thermally setting the textile strands when they are wound about a second mandrel at a second braid angle to determine the nominal sleeve size and shape.

32. The process of claim 31 wherein:

the second mandrel has a diameter greater than that of the first mandrel, and the first and second braid angles are within one degree of one another.

33. The process of claim 31 wherein:

said first and second mandrels have substantially the same diameters, and the first braid angle is larger than the second braid angle.

34. A stent graft formed according to the process of claim 22.

35. The process of claim 22 wherein:

said winding a plurality of textile strands further includes winding the textile strands around a selectively sized mandrel.

36. A process for making a medical device, including:

braiding a tubular stent of open construction including a plurality of structural strands forming multiple first intersections and defining a first braid angle with the tubular stent in a nominal state, wherein the structural strands along the length of the tubular stent are free of bonding to one another at the first intersections, the tubular stent being adjustable between the nominal state and a radially-reduced axially-elongated state according to a first relationship of radial reduction versus axial elongation;

braiding a compliant tubular sleeve including a plurality of compliant textile strands forming multiple second intersections and defining a second braid angle substantially the same as said first braid angle with the tubular sleeve in a nominal state, wherein the textile strands along the length of the tubular sleeve are free of bonding to one another at the second intersections, the tubular sleeve being adjustable between said nominal state and a radially-reduced axially elongated state according to a second relationship of radial reduction versus axial elongation substantially equivalent to said first relationship; and attaching a selected one of the stent and the sleeve within and in an axial alignment with the other of said stent and sleeve so that said other surrounds the selected one.

37. The process of claim 36 further including:

prior to said attaching, applying an adhesive to at least one of the stent and the sleeve over at least a portion of its axial length, wherein said attaching includes maintaining the stent and the sleeve engaged with one another for a time sufficient for the adhesive to bond the stent and the sleeve.

38. The process of claim 36 wherein:

the selected one of the stent and sleeve is the stent, and said attaching includes positioning the stent within and surrounded by the sleeve.

39. The process of claim 36 wherein:

said forming of a tubular stent comprises arranging the structural strands as first and second sets of helices wound in opposite directions to form rhombic interstices between adjacent structural strands; and said forming the tubular sleeve comprises arranging the textile strands as third and fourth sets of helices wound in opposite directions about a common longitudinal axis.

40. The process of claim 36 wherein:

said forming the stent includes heat setting the structural strands when they are wound about a first mandrel at the first braid angle to determine the nominal stent size and shape, and said forming the tubular sleeve includes thermally setting the textile strands when they are wound about a second mandrel at the second braid angle to determine the nominal sleeve size and shape.

41. The process of claim 36 wherein:

said forming a compliant tubular sleeve comprises imparting to the sleeve in the nominal state a diameter and shape substantially the same as a corresponding diameter and shape of the tubular stent in the nominal state.

42. A process for making a medical device, including:

providing a tubular stent adjustable between a nominal state and a radially-reduced axially-elongated state according to a first relationship of radial reduction versus axial elongation;

forming a compliant tubular sleeve of a thermally formable material having substantially the same shape and diameter as the stent in its nominal state, heating the tubular sleeve while it is maintained in said shape and diameter to a heat forming temperature sufficient to thermally impart said shape and diameter to the sleeve when the sleeve is in a nominal state, wherein the sleeve is adjustable between said nominal state and a radially-reduced axially-elongated state according to a second relationship of radial reduction versus axial elongation substantially equivalent to said first relationship, and provides a graft;

disposing a selected one of the stent and the compliant sleeve within and in an axial alignment with the other of the stent and sleeve, so that said other surrounds the selected one, then bringing the stent and sleeve into an engagement; and while maintaining the stent and compliant sleeve in said engagement, binding the stent and sleeve together.

43. The process of claim 42 further including:

applying an adhesive to at least one of the stent and the sleeve over at least a portion of its axial length; and wherein said binding includes maintaining the sleeve and the stent in said engagement for a time sufficient for the adhesive to bond the sleeve and the stent.

44. The process of claim 42 wherein:

said disposing places the stent within and surrounded by the sleeve.

45. The process of claim 42 wherein:

said providing a tubular stent comprises arranging a plurality of structural strands into first and second sets of helices wound in opposite directions about a common longitudinal stent axis, and said forming a tubular sleeve comprises arranging a plurality of textile strands into third and fourth sets of helices wound in opposite directions about a common longitudinal sleeve axis.

46. The process of claim 45 wherein:

said structural strands are thermally formable, and said providing a tubular stent further comprises winding the structural strands around a selectively sized first mandrel, then heating the strands while so wound to a first heat forming temperature sufficient to thermally impart a nominal size and shape for the stent when in its nominal state; and said forming a compliant tubular sleeve comprises winding the textile strands around a selectively sized second mandrel.

* * * * *